US006995291B2

(12) United States Patent
Walther

(10) Patent No.: US 6,995,291 B2
(45) Date of Patent: Feb. 7, 2006

(54) PROCESS FOR THE OXIDATION OF UNSATURATED ALCOHOLS

(75) Inventor: Eric Walther, Geneva (CH)

(73) Assignee: Firmenich SA, Geneva (CH)

( * ) Notice: Subject to any disclaimer, the term of this patent is extended or adjusted under 35 U.S.C. 154(b) by 142 days.

(21) Appl. No.: 10/668,790

(22) Filed: Sep. 22, 2003

(65) Prior Publication Data

US 2004/0064000 A1    Apr. 1, 2004

Related U.S. Application Data

(63) Continuation of application No. PCT/IB03/00139, filed on Jan. 15, 2003.

(30) Foreign Application Priority Data

Jan. 29, 2002    (WO) ...................... PCT/IB02/00304

(51) Int. Cl.
 *C07C 45/00*    (2006.01)
(52) U.S. Cl. ...................... 568/361; 568/363; 568/364; 568/377; 568/403; 568/407; 568/408; 568/446; 568/447; 568/471; 568/476
(58) Field of Classification Search ................. 568/361, 568/363, 364, 377, 403, 407, 408, 446, 447, 568/471, 476
See application file for complete search history.

(56) References Cited

FOREIGN PATENT DOCUMENTS

EP    1 103 537 A1    5/2001

OTHER PUBLICATIONS

Aneli et al., XP-002238208, "Fast and Selective Oxidation of Primary alcohols to Aldehydesor or to Carboxylic Acids and of Secondary Alcohols to Ketones Mediated by Oxoammonium Salts under Two-Phase Conditions", Journal of Org. Chem, vol. 52, No. 12, pp2659-2663 , (1987).

Dijksman et al., XP-002238182, "Polymer immobilised TEMPO (PIPO): an efficient catalyst for the cholorinated hydrocarbon solvent-free and bromide-free oxidation of alcohols with hypochlorite". Chem. Commun. pp 271-271 (2000).

Nooy et al., XP-002072173, On the Use of Stable Organic Nitroxyl Radicals for the Oxidatioen of Primary and Secondary Alcohols, Synthesis, George Thieme Verlag, Stuttgart, DE, PP 1153-1174 (1996).

deNooy et al., XP002072173, "On the Use of Stable Organic Nitroxy Radicals for the Oxidation of Primary and Secondary Alcohols," Sunthesis Geord Thieme Verlag, Stuttgart, DE, pp 1153-1174 (1996).

C. Bolm et al., "TEMPO Oxidations with a Silica-Supported Catalyst," Chem. Commun. , 1999, pp. 1795-1796.

*Primary Examiner*—Sikarl A. Witherspoon
(74) *Attorney, Agent, or Firm*—Winston & Strawn LLP

(57)    ABSTRACT

The present invention relates to the field of organic synthesis and more precisely to a process for the synthesis of an unsaturated aldehyde or ketone by oxidation of the corresponding alcohol. The oxidation is performed by a hypochlorite salt and a catalytic amount of a N-(2,2,6,6-tetraalkyl-4-piperidinyl-N-oxyl)-2-amino-1,3,5-triazine compound, preferably a N-oxyl derivative of one of the polymers known under the trademark Chimassorb® 944 or 2020.

14 Claims, No Drawings

US 6,995,291 B2

PROCESS FOR THE OXIDATION OF UNSATURATED ALCOHOLS

CROSS-REFERENCE TO RELATED APPLICATIONS

This application is a continuation of International Application PCT/IB03/00139 filed Jan. 15, 2003, the entire content of which is expressly incorporated herein by reference thereto.

TECHNICAL FIELD

The present invention relates to the field of organic synthesis and more precisely to a process for the synthesis of an unsaturated aldehyde or ketone by oxidation of the corresponding alcohol. The oxidation is performed by a hypochlorite salt and a catalytic amount of an N-(2,2,6,6-tetraalkyl-4-piperidinyl-N-oxyl)-2-amino-1,3,5-triazine derivative, preferably an N-oxyl derivative of one of the polymers known under the trademark Chimassorb® 944 or 2020 (origin: Ciba Specialty Chemicals, Basel, Switzerland).

BACKGROUND ART

The oxidation of an alcohol into the corresponding aldehyde or ketone by a hypochlorite salt and in the presence of an N-oxyl derivative as catalyst is a very attractive process for the chemical industry as it involves inexpensive and readily available oxidants and catalysts.

However, the prior art in this field proves that only saturated, benzylic or arylalkyl alcohols can be oxidized with good yield using such a process. Indeed, the use of unsaturated alcohols, e.g., those having an alkenyl group, is quite rare and results always in very low yields, if any. Thus, there is a need for improved processes of these types.

SUMMARY OF THE INVENTION

In order to overcome the problems aforementioned, the present invention relates to a catalytic process, with high yields, for the oxidation of unsaturated alcohols allowing the use of a hypochlorite compound as a secondary oxidant.

The process of the invention concerns more specifically the oxidation of an unsaturated alcohol into the corresponding unsaturated aldehyde or ketone in the presence of an effective amount of a hypochlorite salt and a N-(2,2,6,6-tetraalkyl-4-piperidinyl-N-oxyl)- 2-amino-1,3,5-triazine derivative as catalyst. By "unsaturated alcohol" it is meant an alcohol having one or more non-aromatic carbon-carbon double bond.

More precisely, the process of the invention concerns the oxidation of an unsaturated alcohol, or substrate, of formula

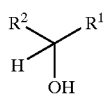
(I)

$R^1$ represents a hydrogen atom, a $C_1$ to $C_{20}$ linear, branched or cyclic saturated or unsaturated hydrocarbon group, said hydrocarbon group optionally being substituted and also optionally including one or two oxygen or nitrogen atoms;

$R^2$ represents a $C_2$ to $C_{20}$ linear, branched or cyclic alkenyl, alkandienyl or alkantrienyl hydrocarbon group, said hydrocarbon group optionally being substituted and also optionally including one or two oxygen or nitrogen atoms; or said $R^1$ and $R^2$ optionally may be bonded together to form an unsaturated ring having 5 to 20 carbon atoms, said ring optionally being substituted and also optionally including one or two oxygen or nitrogen atoms;

wherein the optional substituents of $R^1$, $R^2$ and of the ring which said $R^1$ and $R^2$ together may optionally form, are $C_1$ to $C_{15}$ linear, branched or cyclic alkyl, alkenyl or aromatic groups;

into a corresponding unsaturated aldehyde or ketone of formula

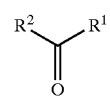
(II)

wherein $R^1$ and $R^2$ are as defined in formula (I);
wherein the oxidation is performed by a hypochlorite salt of formula $$M(OCl)_n \quad (III)$$

in which M represents an alkaline metal, in which case n is 1, or an alkaline-earth metal in which case n is 2;
and in the presence of a catalytic amount of a N-(2,2,6,6-tetraalkyl-4-piperidinyl-N-oxyl)-2-amino-1,3,5-triazine compound.

As optional ingredients, one of a bromide salt of formula M'Br or a bicarbonate of formula M'HCO₃ may be added to the process of the invention, wherein M' is an alkaline metal.

DETAILED DESCRIPTION OF THE PREFERRED EMBODIMENTS

A preferred unsaturated alcohol, and the correspondingly preferred unsaturated aldehyde or ketone, is a compound of formula (I), or (II) respectively, wherein $R^1$ represents a hydrogen atom, a $C_1$ to $C_{15}$ linear, branched or cyclic saturated or unsaturated hydrocarbon group possibly substituted and also possibly comprising one or two oxygen atoms;

$R^2$ represents a $C_2$ to $C_{15}$ linear, branched or cyclic alkenyl, alkandienyl or alkantrienyl hydrocarbon group, possibly substituted and possibly comprising one or two oxygen atoms; or said $R^1$ and $R^2$ may be bonded together to form an unsaturated ring having 5 to 20 carbon atoms, said ring being possibly substituted and possibly comprising one or two oxygen or nitrogen atoms; and the possible substituents of $R^1$, $R^2$ and of the ring which said $R^1$ and $R^2$ may form together, are $C_1$ to $C_{10}$ linear, branched or cyclic alkyl, alkenyl or aromatic groups;

In a particularly attractive embodiment of the invention, the unsaturated alcohol, and the corresponding unsaturated aldehyde, is a compound of formula (I), or (II) respectively, wherein $R^1$ represents a hydrogen atom;

$R^2$ represents a $C_5$ to $C_{15}$ linear, branched or cyclic alkenyl or alkandienyl hydrocarbon group, possibly substituted; or $R^2$ represents a $C_7$ to $C_{15}$ linear, branched or cyclic alkantrienyl hydrocarbon group possibly substituted; and the possible substituents of $R^2$ are $C_1$ to $C_8$ linear, branched or cyclic alkyl, alkenyl or aromatic groups.

The hypochlorite salt is preferably selected from the group consisting of NaOCl, KOCl and Ca(OCl)$_2$.

The bromide salt is preferably KBr or NaBr. Preferred bicarbonates are KHCO$_3$ or NaHCO$_3$.

The N-(2,2,6,6-tetraalkyl-4-piperidinyl-N-oxyl)-2-amino-1,3,5-triazine compound, the catalyst, is preferably a compound of formula

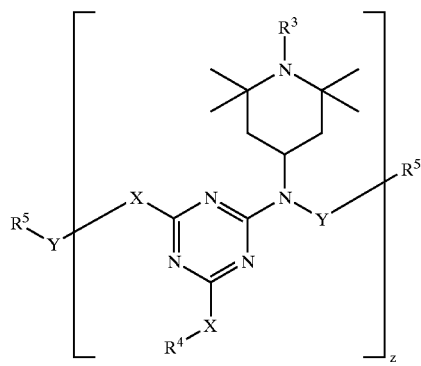

(IV)

wherein z represents an integer from 1 to 20;

$R^3$ represents, simultaneously or independently, a hydrogen atom or an oxyl radical (O), with the proviso that at least one $R^3$ group is an oxyl radical;

X represents an oxygen atom or a —NR$^4$-group;

$R^4$ represents, simultaneously or independently, a hydrogen atom, a 2,2,6,6-tetramethyl-4-piperidinyl group, a 2,2,6,6-tetramethyl-4-piperidinyl-N-oxyl radical group or a C$_1$ to C$_{15}$ linear, branched or cyclic saturated or unsaturated hydrocarbon group, said hydrocarbon group being possibly comprising one or two oxygen or nitrogen atoms; or two $R^4$ groups, bonded to the same nitrogen atom, may be bonded together to form a heterocycle having 5 to 7 members and which may contain an oxygen atom;

$R^5$ represents, simultaneously or independently, a hydrogen atom or a NR$^6_2$ group;

$R^6$ represents, simultaneously or independently, a hydrogen atom, a C$_1$ to C$_{20}$ linear, branched or cyclic saturated or unsaturated hydrocarbon group, a 2,2,6,6-tetramethyl-4-piperidinyl-N-oxyl radical group, a 2,2,6,6-tetramethyl-4-piperidinyl group or a group of formula

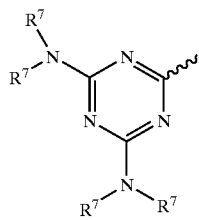

(V)

$R^7$ representing, simultaneously or independently, a hydrogen atom, a C$_1$ to C$_{12}$ linear or branched alkyl group, a 2,2,6,6-tetramethyl-4-piperidinyl-N-oxyl radical group or a 2,2,6,6-tetramethyl-4-piperidinyl group; and Y represents, simultaneously or independently, a C$_2$ to C$_{20}$ linear, branched or cyclic alkylene group possibly comprising one or two oxygen or nitrogen atoms.

More preferably, the catalyst is a polymeric or oligomeric compound of formula

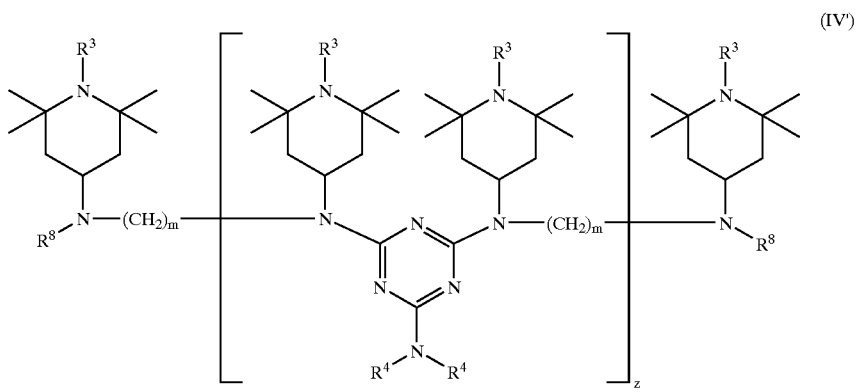

(IV')

wherein z represents an integer from 2 to 10;

m represent an integer from 2 to 12;

$R^3$ is as defined in formula (IV);

$R^4$ represents, simultaneously or independently, a hydrogen atom, a 2,2,6,6-tetramethyl-4-piperidinyl-N-oxyl radical group, a 2,2,6,6-tetramethyl-4-piperidinyl group or a C$_1$ to C$_{10}$ linear or branched alkyl or alkenyl group; or two $R^4$ groups, bonded to the same nitrogen atom, may be bonded together to form a heterocycle having 6 members and which may contain an oxygen atom; and $R^8$ represents, simultaneously or independently, a hydrogen atom, a C$_1$ to C$_{10}$ linear or branched alkyl or alkenyl group, a 2,2,6,6-tetramethyl-4-piperidinyl-N-oxyl radical group, a 2,2,6,6-tetramethyl-4-piperidinyl group or a group of formula (V) as defined previously.

Even more preferably, the catalyst is a N-oxyl derivative of the polymers having the CAS Registry Numbers 71878-19-8 or 192268-64-7 and which are also known under the trademark Chimassorb® 944 or 2020 respectively (origin: Ciba Specialty Chemicals, Basel, Switzerland). One of said derivatives of the Chimassorb® 944 is known in the literature with the name PIPO and has the CAS Registry Number 91993-31-6.

In a general way, the catalyst of formula (IV) can be prepared and isolated prior to its use according to the general methods described in the literature (E. G. Rozantsev et al. in Synthesis 1971, 190, or in the patent application FR 2788272).

Moreover, the catalyst of formula (IV) can be prepared in situ, i.e. in the reaction medium, by using the same methods mentioned herein above without isolation or purification, just before their use.

The catalyst of formula (IV) can be added to the reaction medium in a large range of concentrations. As non-limiting examples, one can cite as catalyst concentration values ranging from 0.02 to 0.15 molar equivalents, relative to the amount of alcohol of formula (I), preferably between 0.03 and 0.1 molar equivalents. It goes without saying that the optimum concentration of catalyst will depend on the nature of the latter and on the alcohol of formula (I) used during the process, and that a person skilled in the art will be able to define said optimum concentration by carrying out routine experiments.

Concerning the quantities of the hypochlorite salt, which can be added to the reaction mixture, one can cite, as non-limiting examples, ranges between 0.9 and 2.5 molar equivalents, relative to the amount of alcohol of formula (I), preferably between 0.9 and 1.5 molar equivalents. In the case the substrate is a primary alcohol, then particularly useful concentrations of hypochlorite salt may range preferably between 1.0 and 1.3 molar equivalents. Again the optimum concentration of hypochlorite salt will depend on the nature of the latter and on the alcohol of formula (I) used during the process, therefore a person skilled in the art will be able to define said optimum concentration by carrying out routine experiments.

The bromide salt M'Br may be added in a quantity ranging between 0 and 0.05 molar equivalents relative to the amount of alcohol of formula (I), preferably between 0.005 and 0.015 molar equivalents.

The bicarbonate M'HCO$_3$ may be added in a quantity ranging between 0 and 0.2 molar equivalents relative to the amount of alcohol of formula (I), preferably between 0.05 and 0.15 molar equivalents.

The oxidation reaction can be carried out in the presence or absence of a solvent. When a solvent is required or used for practical reasons, then any solvent currently used in reactions where an alcohol is oxidized can be employed for the purposes of the invention, provided that the starting alcohol of formula (I) and the N-(2,2,6,6-tetraalkyl-4-piperidinyl-N-oxyl)-2-amino-1,3,5-triazine derivative are at least partially soluble. Non-limiting examples include aromatic solvents such as benzene, toluene or xylene, hydrocarbon solvents such as hexane or cyclohexane, dialkyl ethers such as methyl terbutyl ether, $C_1$ to $C_6$ alkyl acetate such an ethyl or propyl acetate, chlorinated solvents such as dichloromethane or chloroform, or mixtures thereof. A person skilled in the art is well able to select the most convenient solvent in each case to optimize the oxidation reaction, however ethyl or propyl acetate, dichloromethane or toluene is the preferred solvents.

The temperature at which the process of the invention can be carried out may be comprised in a large range of concentrations. As non-limiting examples, one can cite temperature ranging between 0° C. and 60° C., preferably in the range between 15° C. and 40° C. Of course, a person skilled in the art is also able to select the optimum temperature, taking into account, e.g., the melting and boiling point of the catalyst, starting and final products as well as of the solvent.

It is noteworthy that the process according to the invention, in addition to its characteristic high yields, presents also the advantage of producing low quantities of chlorinated by-products, which are frequently undesired impurities, to the contrary of the prior art processes using hypochlorite salts. In general terms, such chlorinated by-products represent less than 5% of yield, and frequently even less than 3%.

EXAMPLES

The invention will now be described in further detail by way of the following examples, wherein the abbreviations have the usual meaning in the art, the temperatures are indicated in degrees centigrade (° C.).

Example 1

Oxidation of Primary Alcohols Containing Double Bonds with NaOCl Catalyzed by PIPO (N-oxyl Derivative of Chimassorb® 944)

PIPO can be obtained according to any of the methods reported in the literature, e.g. the patent application FR 2788272 or Dijksman et al. in Synlett 2001, 102–4.

General Procedure:

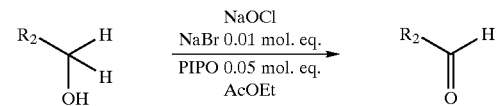

In a 100 ml round bottomed flask were charged PIPO (0.05 molar equivalents) and NaBr (20% aqueous solution; 0.01 molar equivalents) followed by the alcohol to be oxidized (10 g, 1 molar equivalents) and ethyl acetate as solvent (35 g). After dissolution of PIPO, it was introduced over one hour, at room temperature, an aqueous solution containing NaOCl (1.1–1.45 molar equivalents) and in which NaHCO$_3$ (2% weight/weight relative to NaOCl solution) was added just before use. At the end of the introduction, the stirring was continued for 15–45 min and afterwards the reaction mixture was allowed to stand until the phase separation. The aqueous phase was removed, and the organic phase was washed with water. Then, the organic phase was concentrated under vacuum and the clear orange crude product was purified by distillation (bulb-to-bulb) to afford the corresponding aldehyde. The aldehydes obtained had all the same spectroscopic data as reported in the literature.

The results obtained for the oxidation of some unsaturated alcohols are summarized below in Table 1.

TABLE 1

Results of the oxidation of some unsaturated alcohols into the corresponding aldehydes using NaOCl and PIPO as catalyst

| Alcohol a) | Aldehyde a) | Conversion of the alcohol (%) | Yield of the aldehyde (%) | NaOCl b) |
|---|---|---|---|---|
| 1a | 1b | 99.5 | 90 | 1.05 |
| 1a i) | 1b | 79 | 20 | 1.25 |
| 2a | 2b | 100 | 99 | 1.05 |
| 3a | 3b | 97 | 70 | 1.45 |
| 4a ii) | 4b | 99 | 77 | 1.25 |
| 5a | 5b | 89 | 81 | 1.10 |
| 5a iii) | 5b | 86 | 81 | 1.10 |
| 5a iv) | 5b | 55 | — | 1.10 |

TABLE 1-continued

Results of the oxidation of some unsaturated alcohols into the
corresponding aldehydes using NaOCl and PIPO as catalyst

| Alcohol [a] | Aldehyde [a] | Conversion of the alcohol (%) | Yield of the aldehyde (%) | NaOCl [b] |
|---|---|---|---|---|
| 6a | 6b | 98 | 82 | 1.18 |
| 7a | 7b | 90 | 77 | 1.30 |
| 7a [v] | 7b | 5 | — | 1.30 |

[a] alcohol or aldehyde of formula (II) or (I) respectively:
1a: 3-Phenyl-2-propen-1-ol        1b: 3-Phenyl-2-propenal
2a: (E)-2-Dodecen-1-ol            2b: (E)-2-Dodecenal
3a: 3,7-Dimethyl-2,6-octadien-1-ol 3b: 3,7-Dimethyl-2,6-octadienal
4a: (2E,4Z,7Z)-2,4,7-Decatrien-1-ol 4b: (2E,4Z,7Z)-2,4,7-Decatrienal
5a: (Z)-5-Octen-1-ol              5b: (Z)-5-Octenal
6a: 10-Undecen-1-ol               6b: 10-Undecenal
7a: 3-(4-Tert-butyl-1-cyclohexen-1-yl)-1-propanol   7b: 3-(4-Tert-butyl-1-cyclohexen-1-yl)-1-propanal
[b] molar equivalent, relative to the amount of alcohol
[i] in CH2Cl2, in the presence of 0.1 molar equivalent of KBr and with 0.01 molar equivalent of 4-methoxy-2,2,6,6-tetraalkyl-piperidine-N-oxyl (P. L. Anelli, C. Biffi, F. Montanari and S. Quici, J. Org. Chem. 1987, 52, 2559).
[ii] in CH$_2$Cl$_2$, with 0.1 molar equivalent of PIPO.
[iii] in the absence of NaBr.
[iv] with 0.03 molar equivalent of 2,2,6,6-tetraalkyl-piperidine-N-oxyl.
[v] with 0.01–0.1 molar equivalent of 2,2,6,6-tetraalkyl-piperidine-N-oxyl.

Example 2

Oxidation of an Unsaturated Secondary Alcohol with NaOCl Catalyzed by PIPO (N-oxyl Derivative of Chimassorb® 944)

In a 100 ml round bottomed flask were charged PIPO (0.029 molar equivalents) and NaBr (20% aqueous solution; 0.01 molar equivalents) followed by isophorol (5 g, 1 molar equivalents) and ethyl acetate as solvent (13 g). After dissolution of PIPO, it was introduced over approximately one hour, at room temperature, an aqueous solution containing NaOCl (2.0 molar equivalents) and in which NaHCO$_3$ (0.7 g) was added just before use. At the end of the introduction, the stirring was continued for 30 min and afterwards the reaction mixture was allowed to stand until the phase separation. The aqueous phase was removed, and the organic phase was washed with a 5% water solution of ascorbic acid. Then, the organic phase was concentrated under vacuum and the clear yellow crude product was purified by distillation (bulb-to-bulb) to afford the corresponding aldehyde. It was thus obtained isophorone in 62% yield (conversion of the starting material=87%).

What is claimed is:

1. A process for the oxidation of an unsaturated alcohol of formula

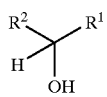

(I)

wherein:
R$^1$ represents a hydrogen atom, a C$_1$ to C$_{20}$ linear, branched or cyclic saturated or unsaturated hydrocarbon group, said hydrocarbon group optionally being substituted and also optionally including one or two oxygen or nitrogen atoms;
R$^2$ represents a C$_2$ to C$_{20}$ linear, branched or cyclic alkenyl, alkandienyl or alkantrienyl hydrocarbon group, said hydrocarbon group optionally being substituted and also optionally including one or two oxygen or nitrogen atoms; or said R$^1$ and R$^2$ optionally may be bonded together to form an unsaturated ring having 5 to 20 carbon atoms, said ring optionally being substituted and also optionally including one or two oxygen or nitrogen atoms; wherein the optional substituents of R$^1$, R$^2$ and of the ring which said R$^1$ and R$^2$ together may optionally form, are C$_1$ to C$_{15}$ linear, branched or cyclic alkyl, alkenyl or aromatic groups;
into a corresponding unsaturated aldehyde or ketone of formula

(II)

wherein R$^1$ and R$^2$ are as defined in formula (I);
wherein the oxidation is performed by a hypochlorite salt of formula $$M(OCl)_n \qquad (III)$$

in which M represents an alkaline metal, in which case n is 1, or an alkaline-earth metal in which case n is 2;
and in the presence of a catalytic amount of a N-(2,2,6,6-tetraalkyl-4-piperidinyl-N-oxyl)-2-amino-1,3,5-triazine compound.

2. The process of claim 1, wherein the unsaturated alcohol is a compound of formula (I),

(I)

wherein:
R$^1$ represents a hydrogen atom;
R$^2$ represents a C$_5$ to C$_{15}$ linear, branched or cyclic alkenyl or alkandienyl hydrocarbon group, that is optionally substituted; or R$^2$ represents a C$_7$ to C$_{15}$ linear, branched or cyclic alkantrienyl hydrocarbon group that is optionally substituted; and
the optional substituents of R$^2$ are C$_1$ to C$_8$ linear, branched or cyclic alkyl, alkenyl or aromatic groups.

3. The process of claim 1, characterized in that the N-(2,2,6,6-tetraalkyl-4-piperidinyl-N-oxyl)-2-amino-1,3,5-triazine is of formula

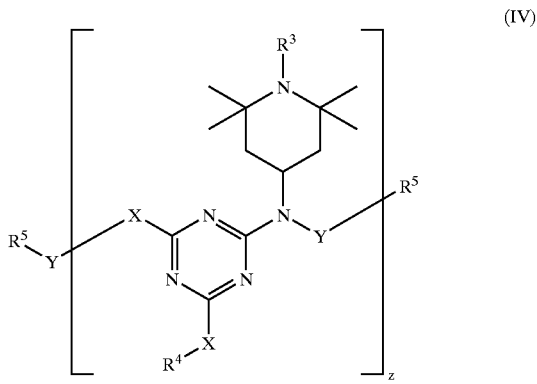

(IV)

wherein z represents an integer from 1 to 20;

$R^3$ represents, simultaneously or independently, a hydrogen atom or an oxyl radical (O.), with the proviso that at least one $R^3$ group is an oxyl radical;

X represents an oxygen atom or a —$NR^4$-group;

$R^4$ represents, simultaneously or independently, a hydrogen atom, a 2,2,6,6-tetramethyl-4-piperidinyl group, a 2,2,6,6-tetramethyl-4-piperidinyl-N-oxyl radical group or a $C_1$ to $C_{15}$ linear, branched or cyclic saturated or unsaturated hydrocarbon group, said hydrocarbon group optionally including one or two oxygen or nitrogen atoms; or two $R^4$ groups, bonded to the same nitrogen atom, may be bonded together to form a heterocycle having 5 to 7 members and which may contain an oxygen atom;

$R^5$ represents, simultaneously or independently, a hydrogen atom or a $NR^6{}_2$ group;

$R^6$ represents, simultaneously or independently, a hydrogen atom, a $C_1$ to $C_{20}$ linear, branched or cyclic saturated or unsaturated hydrocarbon group, a 2,2,6,6-tetramethyl-4-piperidinyl-N-oxyl radical group, a 2,2,6,6-tetramethyl-4-piperidinyl group or a group of formula

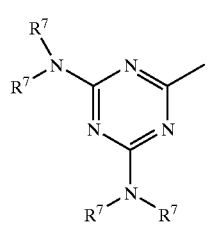

(V)

$R^7$ representing, simultaneously or independently, a hydrogen atom, a $C_1$ to $C_{12}$ linear or branched alkyl group, a 2,2,6,6-tetramethyl-4-piperidinyl-N-oxyl radical group or a 2,2,6,6-tetramethyl-4-piperidinyl group; and Y represents, simultaneously or independently, a $C_2$ to $C_{20}$ linear, branched or cyclic alkylene group optionally including one or two oxygen or nitrogen atoms.

4. The process of claim 3, wherein the N-(2,2,6,6-tetraalkyl-4-piperidinyl-N-oxyl)-2-amino-1,3,5-triazine compound is a polymeric or oligomeric compound of formula

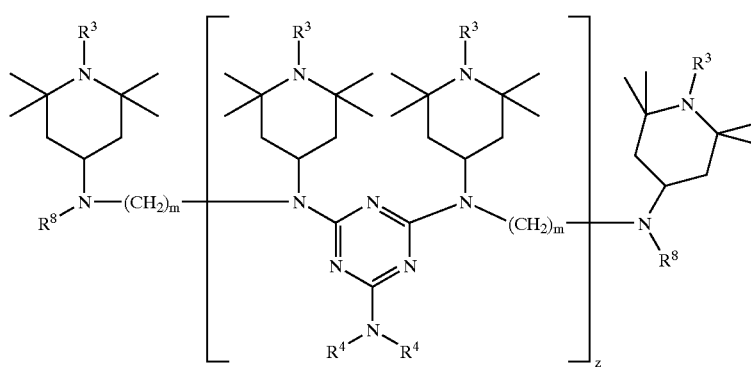

wherein z represents an integer from 2 to 10;
m represents an integer from 2 to 12;
$R^3$ is as defined in claim 3;
$R^4$ represents, simultaneously or independently, a hydrogen atom, a 2,2,6,6-tetramethyl-4-piperidinyl-N-oxyl radical group, a 2,2,6,6-tetramethyl-4-piperidinyl group or a $C_1$ to $C_{10}$ linear or branched alkyl or alkenyl group; or two $R^4$ groups, bonded to the same nitrogen atom, may be bonded together to form a heterocycle having 6 members and which may contain an oxygen atom; and $R^8$ represents, simultaneously or independently, a hydrogen atom, a $C_1$ to $C_{10}$ linear or branched alkyl or alkenyl group, a 2,2,6,6-tetramethyl-4-piperidinyl-N-oxyl radical group, a 2,2,6,6-tetramethyl-4-piperidinyl group or a group of formula (V).

5. The process of claim 4, wherein the N-(2,2,6,6-tetraalkyl-4-piperidinyl-N-oxyl)-2-amino-1,3,5-triazine derivative is a N-oxyl derivative of the polymers having the CAS Registry Numbers 71878-19-8 or 192268-64-7.

6. The process of claim 1, wherein the hypochlorite salt is selected from the group consisting of NaOCl, KOCl and $Ca(OCl)_2$.

7. The process of claim 1, wherein one of a bromide salt of formula M'Br or a bicarbonate of formula $M'HCO_3$ is added to the process, wherein M' is an alkaline metal.

8. The process of claim 1, wherein a bromide salt of KBr or NaBr is added to the process.

9. The process of claim 1, wherein a bicarbonate of $KHCO_3$ or $NaHCO_3$ is added to the process.

10. The process of claim 1, wherein the catalyst has a concentration ranging from 0.02 to 0.15 molar equivalents relative to the amount of alcohol.

11. The process of claim 1, wherein the hypochlorite salt is added to the reaction mixture in an amount of between 0.9 and 2.5 molar equivalents relative to the amount of alcohol.

12. The process of claim 1, which is carried out at a temperature ranging between 0° C. and 60° C.

(IV')

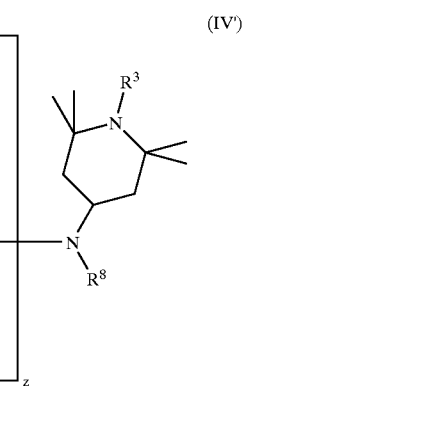

13. The process of claim 1, conducted in a solvent.

14. The process of claim 1, conducted in the absence of a solvent.

* * * * *

UNITED STATES PATENT AND TRADEMARK OFFICE
CERTIFICATE OF CORRECTION

PATENT NO. : 6,995,291 B2
DATED : February 7, 2006
INVENTOR(S) : Walther

It is certified that error appears in the above-identified patent and that said Letters Patent is hereby corrected as shown below:

Title page,
Item [56], References Cited, OTHER PUBLICATIONS,
"Aneli et al." reference, change "Aneli" to -- Anelli --; change "Aldehydesor" to -- Aldehydes or --; and change "pp2659-2663" to -- pp 2559-2663 --.
"Dijksman et al" reference, change "cholorinated" to -- chlorinated --; and change "pp 271-271" to -- pp 271-272 --.
"Nooy et al." reference, delete in its entirety.
"deNooy et al." reference, change "deNooy" to -- de Nooy --; change "Nitroxy" to -- Nitroxyl --; change "Sunthesis George" to -- Synthesis , Georg -- ; and change "PP 1153-1174" to -- pp 1153-1176 --.

Column 9,
Line 2, change "(O.)" to -- (O·) --.

Signed and Sealed this

Eighteenth Day of April, 2006

JON W. DUDAS
*Director of the United States Patent and Trademark Office*